(12) United States Patent
Vaudant et al.

(10) Patent No.: US 7,931,686 B2
(45) Date of Patent: *Apr. 26, 2011

(54) SMALL INCISION INTRAOCULAR LENS WITH ANTI-PCO FEATURE

(75) Inventors: Jerome Vaudant, Rochester, NY (US); Gary A. Richardson, Dallas, TX (US); Griffith E. Altmann, Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/494,489

(22) Filed: Jun. 30, 2009

(65) Prior Publication Data

US 2009/0265000 A1    Oct. 22, 2009

Related U.S. Application Data

(63) Continuation of application No. 11/025,405, filed on Dec. 29, 2004, now Pat. No. 7,569,073.

(51) Int. Cl.
*A61F 2/16*    (2006.01)
(52) U.S. Cl. .................................................. 623/6.17
(58) Field of Classification Search ......... 623/6.16–6.46
See application file for complete search history.

(56) References Cited

U.S. PATENT DOCUMENTS

| | | |
|---|---|---|
| 3,996,187 A | 12/1976 | Travnicek |
| 3,996,189 A | 12/1976 | Travnicek |
| 4,190,693 A | 2/1980 | Martorano et al. |
| 4,244,060 A | 1/1981 | Hoffer |
| 4,418,165 A | 11/1983 | Polmanteer et al. |
| 4,562,600 A | 1/1986 | Ginsberg et al. |
| 4,629,462 A | 12/1986 | Feaster |
| 4,647,282 A | 3/1987 | Fedorov et al. |
| 4,868,251 A | 9/1989 | Reich et al. |
| 5,074,875 A | 12/1991 | Donn et al. |
| 5,171,320 A | 12/1992 | Nishi |
| 5,512,609 A | 4/1996 | Yang |
| 5,549,670 A | 8/1996 | Young et al. |
| 5,620,013 A | 4/1997 | Bretton |
| 5,623,029 A | 4/1997 | Yang |
| 5,693,093 A | 12/1997 | Woffinden et al. |
| 5,693,094 A | 12/1997 | Young et al. |
| 6,051,024 A | 4/2000 | Cumming |
| 6,162,248 A | 12/2000 | Neuhann |
| 6,162,249 A | 12/2000 | Deacon et al. |
| 6,190,410 B1 | 2/2001 | Lamielle et al. |

(Continued)

FOREIGN PATENT DOCUMENTS

DE    19501444 A1    7/1996

(Continued)

OTHER PUBLICATIONS

Nishi, "Posterior Capsule Opacification," Journal of Cataract & Refractive Surgery, (Jan. 1, 1999).

(Continued)

*Primary Examiner* — Suzette J Gherbi
(74) *Attorney, Agent, or Firm* — Jeffrey B. Powers

(57) ABSTRACT

A thin intraocular lens for inhibiting posterior capsular opacification (PCO) includes an optic having an anterior concave region, a posterior concave region, a sharp edge which extends posteriorly and between the posterior concave region and at least a portion of an outer-most peripheral edge surface.

20 Claims, 4 Drawing Sheets

U.S. PATENT DOCUMENTS

| | | |
|---|---|---|
| 6,200,344 B1 | 3/2001 | Lamielle et al. |
| 6,228,115 B1 | 5/2001 | Hoffmann et al. |
| 6,245,106 B1 | 6/2001 | Makker et al. |
| 6,258,123 B1 | 7/2001 | Young et al. |
| 6,267,784 B1 | 7/2001 | Benz et al. |
| 6,277,940 B1 | 8/2001 | Niwa et al. |
| 6,322,589 B1 | 11/2001 | Cumming |
| 6,326,448 B1 | 12/2001 | Ojio et al. |
| 6,398,809 B1 | 6/2002 | Hoffmann et al. |
| 6,406,494 B1 | 6/2002 | Laguette et al. |
| 6,409,762 B1 | 6/2002 | Pynson et al. |
| 6,461,384 B1 | 10/2002 | Hoffmann et al. |
| 6,465,588 B1 | 10/2002 | Li |
| 6,468,306 B1 | 10/2002 | Paul et al. |
| 6,468,307 B1 | 10/2002 | Baikoff et al. |
| 6,555,030 B1 | 4/2003 | Weinschenk, III |
| 6,558,419 B1 | 5/2003 | Pham et al. |
| 6,558,420 B2 | 5/2003 | Green |
| 6,656,222 B2 | 12/2003 | Young et al. |
| 6,800,091 B2 | 10/2004 | Callahan et al. |
| 6,884,262 B2 | 4/2005 | Brady et al. |
| 6,926,744 B1 | 8/2005 | Bos et al. |
| 7,569,073 B2 * | 8/2009 | Vaudant et al. ............ 623/6.17 |
| 2002/0087210 A1 | 7/2002 | Stenger et al. |
| 2002/0095211 A1 | 7/2002 | Young |
| 2002/0103537 A1 | 8/2002 | Willis et al. |
| 2002/0161434 A1 | 10/2002 | Laguette et al. |
| 2003/0055498 A1 | 3/2003 | Paul et al. |
| 2003/0060879 A1 | 3/2003 | Paul et al. |
| 2003/0114926 A1 | 6/2003 | Paul et al. |
| 2003/0120342 A1 | 6/2003 | Green |
| 2003/0171807 A1 | 9/2003 | Pham et al. |
| 2003/0195621 A1 | 10/2003 | Young |
| 2004/0002757 A1 | 1/2004 | Lai et al. |
| 2004/0024454 A1 | 2/2004 | Toop |
| 2004/0059414 A1 | 3/2004 | Green |
| 2005/0107874 A1 | 5/2005 | Assia |
| 2005/0125055 A1 | 6/2005 | Deacon et al. |
| 2005/0125056 A1 | 6/2005 | Deacon et al. |
| 2005/0125057 A1 | 6/2005 | Cumming |
| 2005/0177230 A1 | 8/2005 | Young |
| 2005/0187621 A1 | 8/2005 | Brady |
| 2006/0122700 A1 | 6/2006 | Kurosaka et al. |
| 2007/0027539 A1 | 2/2007 | Pynson |

FOREIGN PATENT DOCUMENTS

| | | |
|---|---|---|
| DE | 29710967 U1 | 10/1997 |
| EP | 0134489 A1 | 3/1985 |
| EP | 0391452 B1 | 1/1994 |
| EP | 0579528 | 1/1994 |
| EP | 0592813 | 4/1994 |
| EP | 0766952 | 4/1997 |
| EP | 1273275 A2 | 1/2003 |
| EP | 0957826 B1 | 8/2003 |
| EP | 1194084 B1 | 12/2004 |
| EP | 1543799 A1 | 6/2005 |
| FR | 2668922 A1 | 5/1992 |
| RU | 1811395 A3 | 4/1993 |
| WO | WO 83/01566 A1 | 5/1983 |
| WO | WO 96/35397 A1 | 11/1996 |
| WO | WO 97/41805 A1 | 11/1997 |
| WO | WO 01/81075 A2 | 11/2001 |
| WO | WO 03/015668 A1 | 2/2003 |
| WO | WO 03/077803 A1 | 9/2003 |
| WO | WO 2004/010895 A2 | 2/2004 |
| WO | WO 2005/032427 A1 | 4/2005 |
| WO | WO 2005/055875 A2 | 6/2005 |
| WO | WO 2005/115278 A1 | 12/2005 |

OTHER PUBLICATIONS

Nishi et al., "Explanation of Endocapsule Posterior Chamber Lens After Spontaneous Posterior Dislocation," Journal of Cataract & Refractive Surgery, p. 273, (Mar. 1, 1996).

Izak et al., "Loop Memory of Haptic Materials in Posterior Chamber Intraocular Lenses," ASCRS Publication, vol. 28 ( No. 7).

International Search Report (PCTISA/210) and Written Opinion (PCT/ISA/237) mailed on Nov. 9, 2004.

* cited by examiner

SMALL INCISION INTRAOCULAR LENS WITH ANTI-PCO FEATURE

RELATED APPLICATION

This application is a continuation of application Ser. No. 11/025,405, filed on Dec. 29, 2004. Said Application is hereby incorporated by reference in its entirety.

BACKGROUND OF THE INVENTION

The present invention relates to intraocular lenses (IOLs) for implantation in an aphakic eye where the natural lens has been removed due to damage or disease (e.g., a cataractous lens). The present invention more particularly relates to a novel IOL designed in a first aspect to be inserted through a sub-3 mm incision made in the eye, and in a second aspect includes a sharp posterior edge to inhibit unwanted growth of lens epithelial cells (hereinafter "LECs") between the IOL and posterior capsular bag, also known as posterior capsule opacification (hereinafter "PCO").

A common and desirable method of treating a cataract eye is to remove the clouded, natural lens and replace it with an artificial IOL in a surgical procedure known as cataract extraction. In the extracapsular extraction method, the natural lens is removed from the capsular bag while leaving the posterior part of the capsular bag (and preferably at least part of the anterior part of the capsular bag) in place within the eye. In this instance, the capsular bag remains anchored to the eye's ciliary body through the zonular fibers. In an alternate procedure known as intracapsular extraction, both the lens and capsular bag are removed in their entirety by severing the zonular fibers and replaced with an IOL which must be anchored within the eye absent the capsular bag. The intracapsular extraction method is considered less attractive as compared to the extracapsular extraction method since in the extracapsular method, the capsular bag remains attached to the eye's ciliary body and thus provides a natural centering and locating means for the IOL within the eye. The capsular bag also continues its function of providing a natural barrier between the aqueous humor at the front of the eye and the vitreous humor at the rear of the eye.

One known problem with extracapsular cataract extraction is posterior capsule opacification, or secondary cataract, where proliferation and migration of lens epithelial cells occur along the posterior capsule behind the IOL posterior surface which creates an opacification of the capsule along the optical axis. This requires subsequent surgery, such as an Er:YAG laser capsulotomy, to open the posterior capsule and thereby clear the optical axis. Undesirable complications may follow the capsulotomy. For example, since the posterior capsule provides a natural barrier between the back of the eye vitreous humor and front of the eye aqueous humor, removal of the posterior capsule allows the vitreous humor to migrate into the aqueous humor which can result in serious, sight-threatening complications. It is therefore highly desirable to prevent posterior capsule opacification in the first place and thereby obviate the need for a subsequent posterior capsulotomy.

One method for preventing PCO is to create a sharp, discontinuous bend in the posterior capsule wall which is widely recognized by those skilled in the art as an effective method for minimizing PCO. See, for example, *Posterior Capsule Opacification* by Nishi, *Journal of Cataract & Refractive Surgery*, Vol. 25, January 1999. This discontinuous bend in the posterior capsule wall can be created using an IOL having a sharp posterior edge.

Another PCO prevention method uses an LEC-targeted pharmaceutical agent. See, for example, U.S. Pat. No. 5,620,013 to Bretton entitled "Method For Destroying Residual Lens Epithelial Cells". While this approach is logical in theory, putting such a method into clinical practice is difficult due to complications arising, for example, from the toxicity of some of the LEC inhibiting agents themselves (e.g., saporin), as well as the difficulty in ensuring a total kill of all LECs in the capsular bag. Any remaining LECs may eventually multiply and migrate over the IOL, eventually resulting in PCO despite the attempt at LEC removal at the time of surgery.

By far the most promising method for inhibiting LEC formation on the posterior surface of an IOL is by designing the IOL to have a sharp peripheral edge particularly at the posterior surface to create a discontinuous bend in the posterior capsule wall. This discontinuous bend in the posterior capsule wall has been clinically proven to inhibit the growth and migration of LECs past this bend and along the IOL surface. One of the early reports of this PCO-inhibiting effect of a planoconvex IOL may be found in *Explanation of Endocapsule Posterior Chamber Lens After Spontaneous Posterior Dislocation* by Nishi et al, *J Cataract & Refractive Surgery*—Vol 22, March 1996 at page 273 wherein the authors examined an explanated planoconvex PMMA IOL where the posterior surface of the IOL was planar and formed a square edge with the peripheral edge of the IOL:

"Macroscopic view of the explanted IOL and capsule revealed a 9.5 mm capsule diameter. The open circular loops fit well along the capsule equator. The capsule equator not in contact with the haptic was also well maintained (FIG. 3). An opaque lens mass (Soemmering's ring cataract) was seen between the haptics and optic. The posterior capsule facing the IOL optic was clear. Histopathological examination of the explanted capsule revealed few epithelial cells (LECs) on the posterior capsule. Between the loops and the optic, a lens mass with accumulation at the edge of the optic was seen (FIG. 4). There was an obvious bend in the posterior capsule at this site." (Emphasis added.)

Thus, in the years since this report, the industry has seen much activity on creating IOLs with a sharp posterior edge so as to create a sharp, discontinuous bend in the posterior capsule wall.

Another trend in modern day cataract surgery is to reduce the corneal incision size as much as possible. This is because larger incision sizes have been attributed to unwanted post-surgical conditions such as incision-induced astigmatism, for example. IOLs and IOL injectors capable of successfully injecting the IOL through a sub 3-mm incision is desirable to most present-day cataract surgeons. Since the IOL must undergo compression and other forces as it is passed through the IOL injector and injected into the eye, the dimensions (particularly the cross-section) of the IOL must accordingly be minimized. An IOL designer is thus further challenged in making an IOL which on the one hand will have the strength and stability to remain centered in the eye, and on the other hand have small enough dimensions to pass through a sub-3 mm injector and into the eye. It will be appreciated that these are often competing design goals in that reducing IOL dimensions to fit through a smaller incision can result in a decrease in the strength and stability of the IOL in the eye. The strength and stability of the IOL within the eye is of course crucial in obtaining and maintaining the intended vision correction afforded by the IOL. Thus, an IOL designer cannot reduce IOL dimensions without first understanding and then compensating, through careful design, the effect such downsizing in dimensions has on the strength and stability of the IOL.

There therefore remains a need for an improved IOL design and method which addresses the problem of LEC migration and subsequent PCO formation, is dimensioned to fit through a sub-3 mm injector, and is strong and stable enough to remain properly positioned in an eye.

SUMMARY OF THE INVENTION

An aspect of the invention is directed to an intraocular lens for implanting in a human eye, comprising a lens optic having opposite anterior and posterior optic surfaces and an optical axis extending from said anterior surface to said posterior surface, a posterior concave region located radially outwardly of said posterior optic surface, an anterior concave region located radially outwardly of said anterior optic surface, an outer-most peripheral edge surface located radially outwardly of said anterior and posterior concave regions, and a posterior sharp edge disposed between the posterior concave region and at least a portion of the outer-most peripheral edge. The lens has a minimum distance between the posterior concave region and the anterior concave region, the minimum distance being less than a second thickness of the lens at a second location that is disposed radially outwardly of the location of the minimum distance.

In some embodiments the lens comprises at least one haptic extending from said outer-most peripheral edge. In some embodiments, the lens comprises an anterior edge surface extending substantially perpendicular to said optical axis between said anterior concave region and said outer-most peripheral edge surface.

Another aspect of the invention is directed to an intraocular lens for implanting in a human eye, comprising a lens optic having opposite anterior and posterior optic surfaces and an optical axis extending from said anterior surface to said posterior surface, a posterior concave region located radially outwardly of said posterior optic surface, an anterior concave region located radially outwardly of said anterior optic surface, an outer-most peripheral edge surface located radially outwardly of said anterior and posterior concave regions, and a posterior sharp edge disposed between the posterior concave region and at least a portion of the outer-most peripheral edge. The lens has a minimum distance between the posterior concave region and the anterior concave region, the minimum distance being less than a second thickness of the lens at a second location that is disposed radially outwardly of the location of the minimum distance.

DETAILED DESCRIPTION

Figure 1:
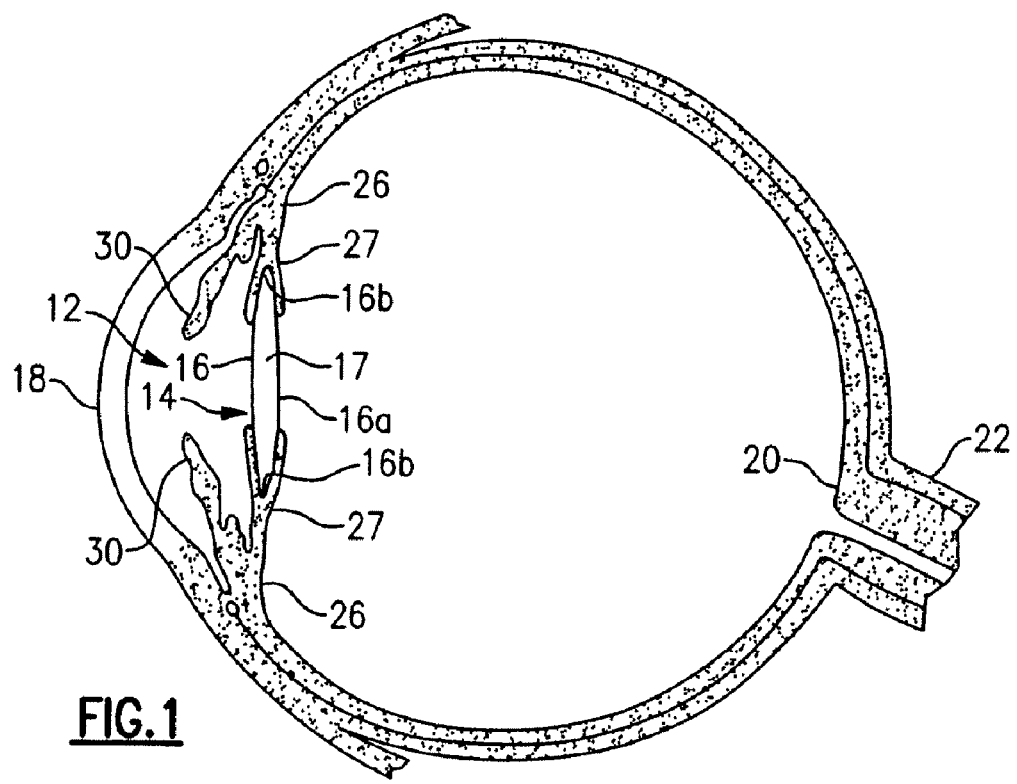
FIG. 1 is a cross-sectional view of a human eye showing the natural lens within the capsular bag of the eye.

Referring now to the drawing, there is seen in FIG. 1 a cross-sectional view of a human eye 10 having an anterior chamber 12 and a posterior chamber 14 separated by the iris 30. Within the posterior chamber 14 is a capsule 16 which holds the eye's natural crystalline lens 17. Light enters the eye by passing through the cornea 18 to the crystalline lens 17 which act together to direct and focus the light upon the retina 20 located at the back of the eye. The retina connects to the optic nerve 22 which transmits the image received by the retina to the brain for interpretation of the image.

In an eye where the natural crystalline lens has been damaged (e.g., clouded by cataracts), the natural lens is no longer able to properly focus and direct incoming light to the retina and images become blurred. A well known surgical technique to remedy this situation involves removal of the damaged crystalline lens which may be replaced with an artificial lens known as an intraocular lens or IOL such as prior art IOL 24 seen in FIG. 2. Although there are many different IOL designs as well as many different options as to exact placement of an IOL within an eye, the present invention concerns itself with an IOL for implanting inside the substantially ovoid-shaped capsule 16 of eye 10. This implantation technique is commonly referred to in the art as the "in-the-bag" technique. In this surgical technique, a part of the anterior portion of the capsular bag is cut away (termed a "capsularhexis") while leaving the posterior capsule 16a intact and still secured to the ciliary body 26.

Thus, in the "in-the-bag" technique of IOL surgery, the IOL is placed inside the capsule 16 which is located behind the iris 30 in the posterior chamber 14 of the eye. An IOL includes a central optic portion 24a which simulates the extracted natural lens by directing and focusing light upon the retina, and further includes a means for securing the optic in proper position within the capsular bag. A common IOL structure for securing the optic is called a haptic which is a resilient structure extending radially outwardly from the periphery of the optic. In a common IOL design, two haptics 24b, 24c extend from opposite sides of the optic and curve to provide a biasing force against the inside of the capsule which secures the optic in the proper position within the capsule.

Figure 2:
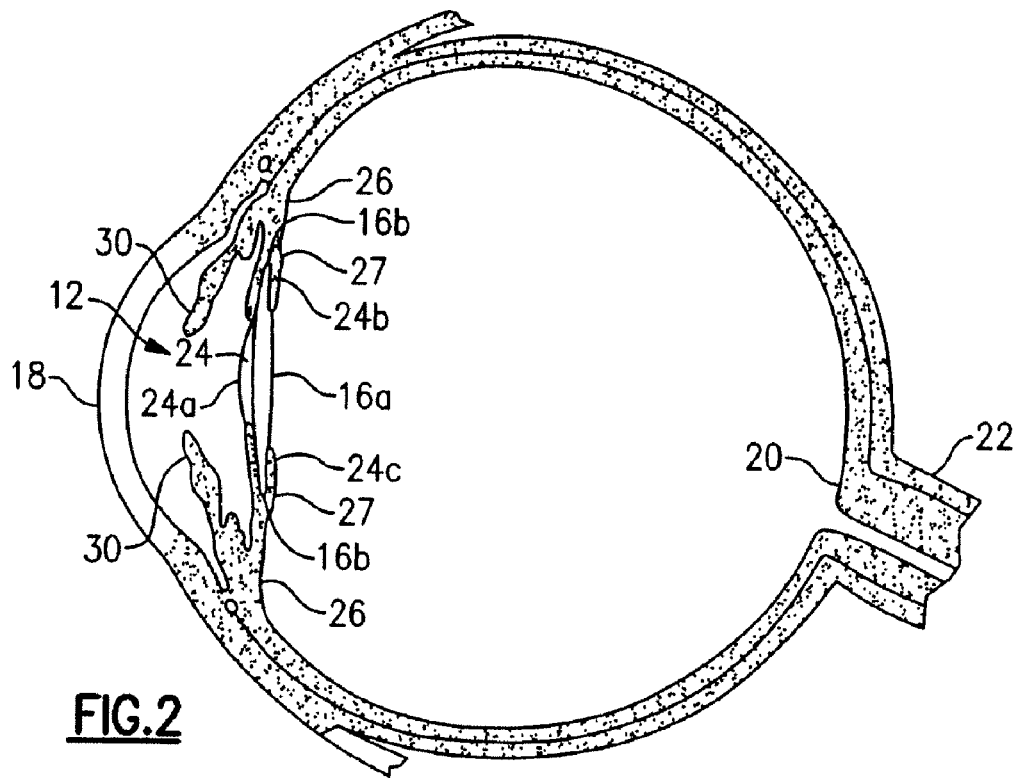
FIG. 2 is a cross-sectional view of a human eye showing the natural lens removed and replaced with a prior art IOL.
Figure 3:
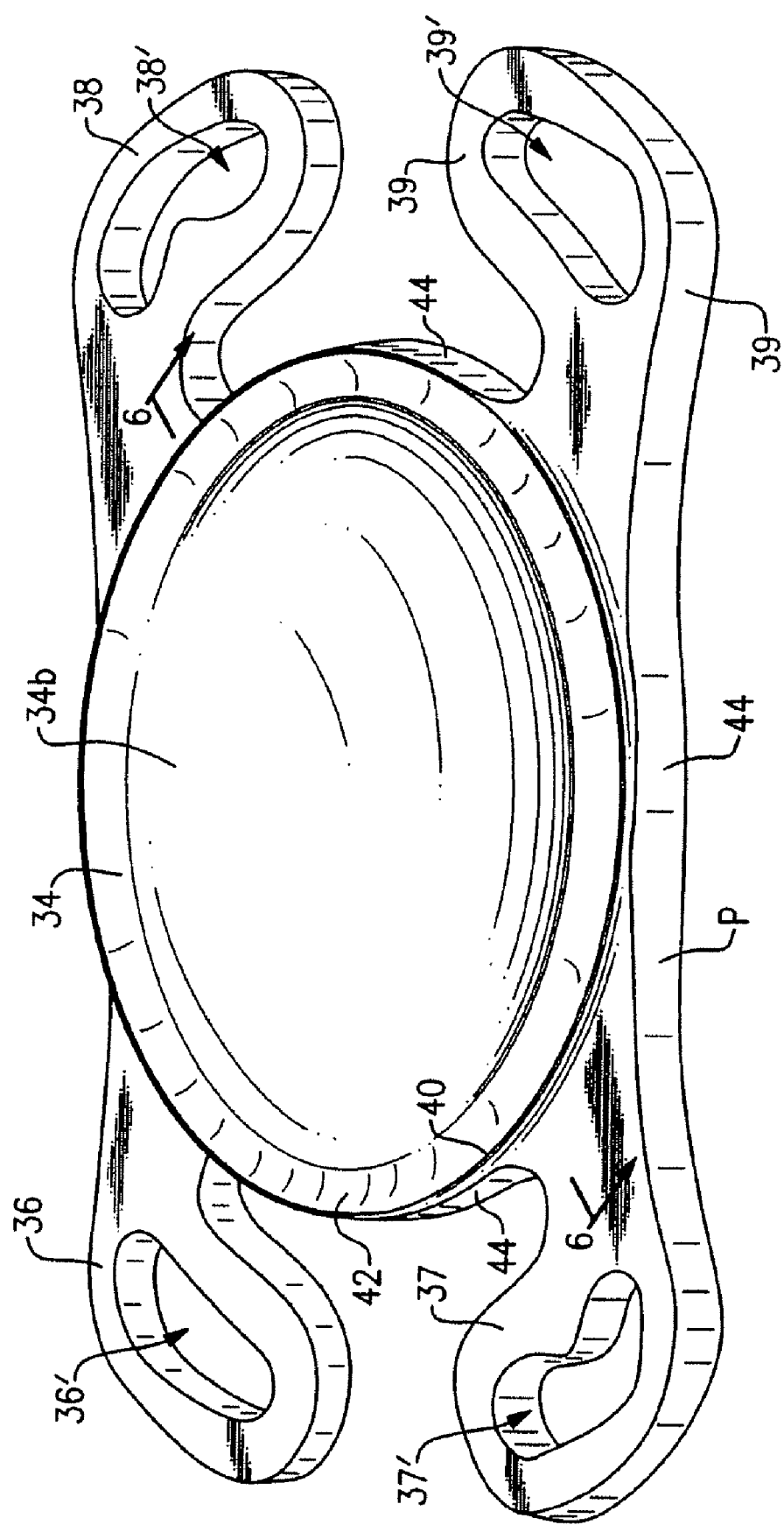
FIG. 3 is a perspective view of an embodiment of the inventive IOL with the posterior optic surface thereof facing upwardly.
Figure 4:
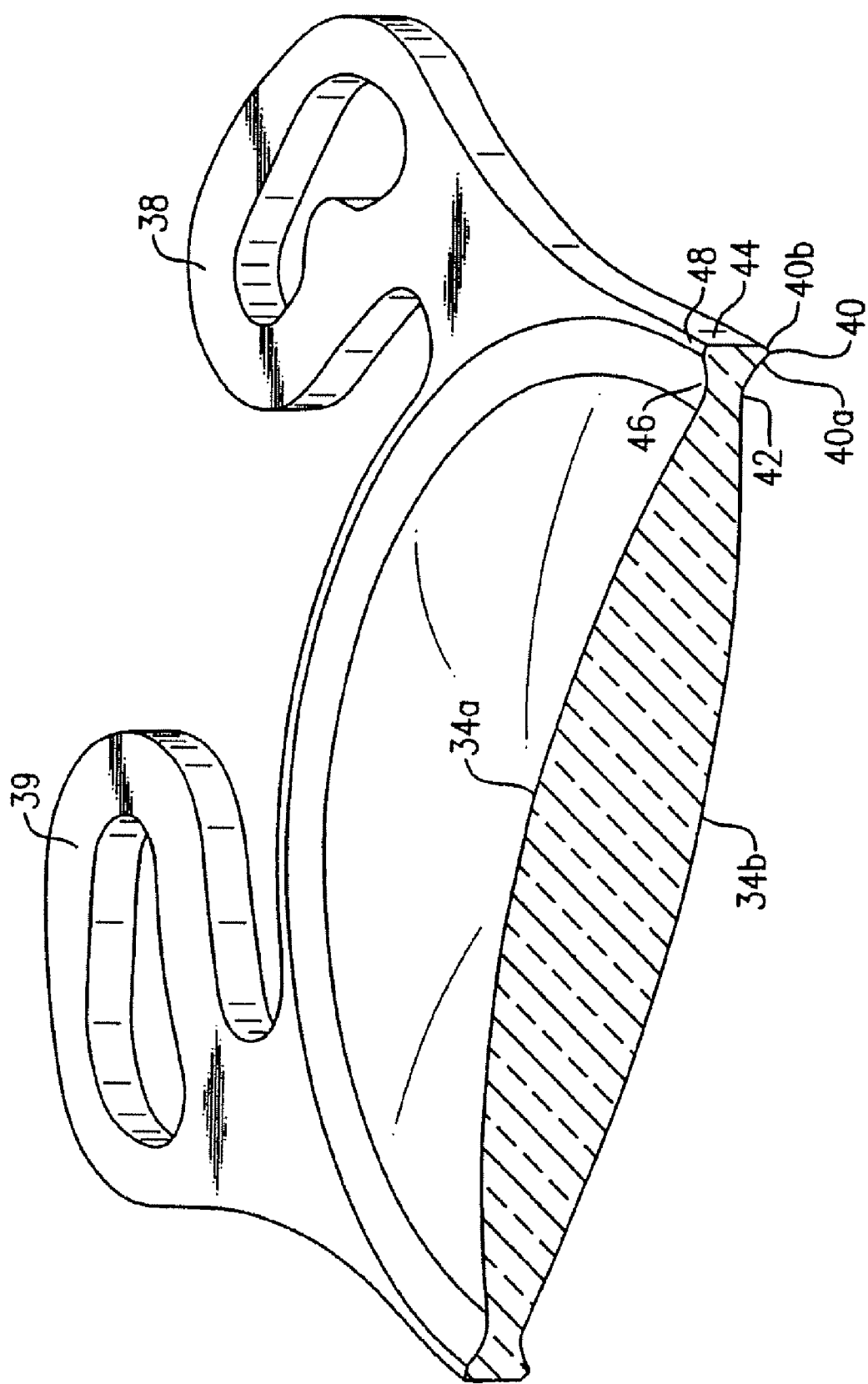
FIG. 4 is a cross-sectional view of the IOL as taken generally along the line 4-4 of FIG. 3.

As stated in the Background section hereof, an undesirable post-surgical condition known as posterior capsule opacification or PCO may occur which results in an implanted IOL becoming clouded and thus no longer able to properly direct and focus light therethrough. The main cause for this condition is the mitosis and migration of lens epithelial cells (LECs) across the posterior surface of the capsule behind the IOL optic. As seen in FIG. 2, the posterior surface 16a of the capsule 16 touches the posterior surface of the IOL optic 24a. When the damaged natural lens is surgically removed, a number of LECs may remain within the capsule 16, particularly at the equator 16b thereof which is the principle source of germinal LECs. Although a surgeon may attempt to remove all LECs from the capsular bag at the time of IOL implantation surgery, it is nearly impossible to remove every single LEC. Any remaining LECs can multiply and migrate along the posterior capsule wall 16a. This is especially true in IOLs having rounded edges, where it has been found that clinically significant PCO results in about 20%-50% of patients three years post surgery. A presently popular and effective method of preventing PCO is to create a sharp, discontinuous bend in the posterior capsule wall 16a as explained in the Background section hereof.

Referring now to FIGS. 3-6, an exemplary embodiment of the inventive IOL 32 is shown. IOL 32 is seen to include a central optic portion 34 having opposite anterior and posterior surfaces 34a and 34b, respectively. When implanted within the eye, anterior optic surface 34a faces the cornea 18 and posterior optic surface 34b faces the retina 20. In the exemplary embodiment, a total of four haptics 36-39 are attached to and extend from optic portion 34 and are configured to provide a biasing force against the interior of the capsule 16 to properly position IOL 32 therein. More particularly, the haptics 36-39 are configured such that upon implanting the IOL with the capsular bag, the haptics engage the interior surface of the capsular bag. The engagement between the haptics and capsule creates a biasing force causing the IOL optic 34 to vault posteriorly toward the retina 20 whereupon the posterior surface 34b of the IOL optic presses tightly against the interior of the posterior capsule wall 16a of capsule 16.

It is noted that the number and configuration of the haptics may vary and are within the scope of the invention. Furthermore, IOL 32 may be made from any suitable IOL material, e.g., PMMA, silicone, acrylics, hydrogels, and combinations thereof. The IOL 32 may also be a one piece (e.g., where the optics and haptics are formed from a single piece of material) or multiple piece design (e.g. where the haptics are attached to the optic after the optic is formed). In one preferred embodiment, the IOL is lathed as a single piece from a button of intraocular grade acrylic as discussed more fully below.

Referring still to FIGS. 3-6, it is seen that IOL optic 34 has a periphery including a posteriorly facing sharp edge 40 which is effective for inhibiting PCO by creating a bend in the posterior capsule wall when the IOL 32 is implanted in the eye capsule as explained above. Sharp edge 40 is defined at the apex of angle "A" which, in turn, is defined by first and second surfaces 40a, 40b. Angle "A" is preferably between about 70 and 120 degrees, is more preferably between about 80 and 100 degrees, and most preferably is about 90 degrees. The apex of sharp edge 40 lies along an apex axis AA which extends substantially parallel to the optical axis OA. First surface 40a smoothly blends into a posterior concave region 42 which, in turn, smoothly blends into the posterior optic surface 34b. The posterior optic surface 34b of course contributes to the patient's vision and may be of any desired optical design including, for example, spherical, aspherical, toric, multifocal, accommodating (including the dual optic type), and combinations thereof.

Figure 5:
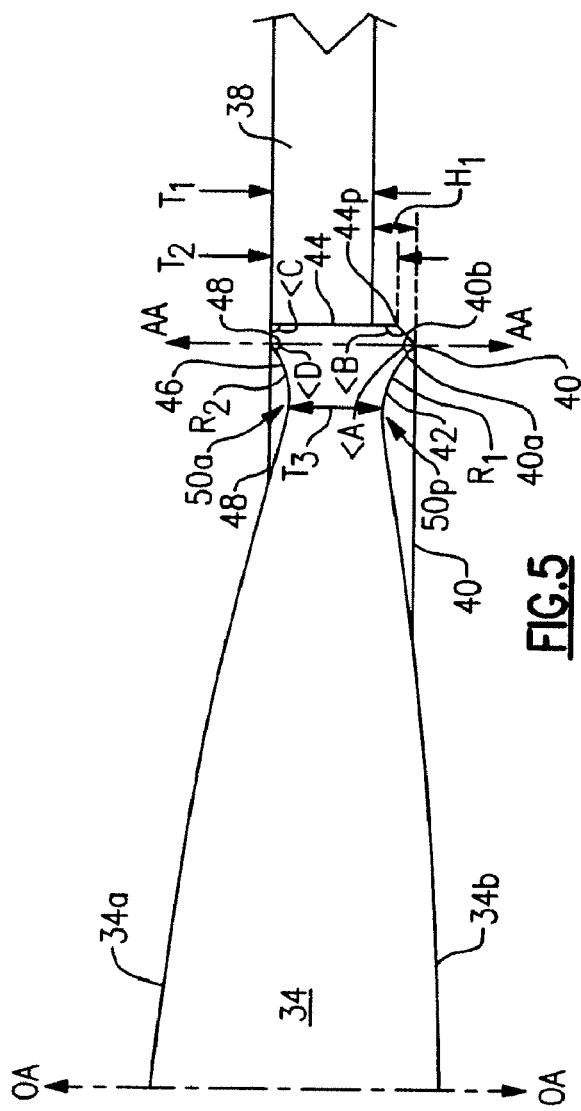
FIG. 5 is an enlarged cross-sectional view of FIG. 6 showing half the IOL to illustrate the edge detail.

The periphery of the optic posterior surface 34b begins where the posterior concave region 42 begins to straighten as it extends radially inwardly, this area being designated 50p in FIG. 5.

The second sharp edge surface 40b intersects the outer-most peripheral edge surface 44 and together therewith forms an obtuse angle "B" which is preferably between about 110 and 150 degrees, is more preferably between about 120 and 140 degrees, and most preferably is about 130 degrees. Outer-most peripheral edge surface 44 is thus located radially outwardly of sharp edge 40 and extends substantially parallel to the optical axis OA and thus also apex axis AA. One or more haptics such as haptics 36-39 extend from the outer-most peripheral edge surface 44 to properly locate the IOL optic 34 in the capsular bag of the patient's eye. In the illustrated embodiment, haptic thickness $T_1$ is preferably between about 0.20 mm and 0.40 mm, is more preferably between about 0.25 mm and 0.35 mm, and is most preferably about 0.30 mm. Haptic thickness $T_1$ is less than the thickness $T_2$ of the outer-most peripheral edge surface 44 which is preferably between about 0.25 mm and 0.50 mm, is more preferably between about 0.30 mm and 0.40 mm, and is most preferably about 0.37 mm. The haptics are also preferably spaced from the posterior limit 44p of the outer-most peripheral edge 44, i.e. the intersection of surface 40b and peripheral edge surface 44. The height $H_1$ of the PCO barrier created by sharp posterior edge 40 as measured from the apex thereof to the haptic is preferably between about 0.05 mm and 0.25 mm, is more preferably between about 0.10 mm and 0.20 mm, and is most preferably about 0.13 mm.

As stated above, the haptics help stabilize the IOL in the eye and cause optic 34 to vault posteriorly such that the sharp edge 40 firmly indents into the posterior capsular wall 16a. To maintain stability and further discourage the IOL vaulting in an anterior direction, an anterior concave region 46 is provided on the anterior surface of the IOL. This anterior concave region 46 is located radially outwardly of and smoothly blends with the anterior optic surface 34a at or near their meeting point 50a. Anterior concave region 46 extends radially outwardly and intersects anterior peripheral edge surface 48 in the opposite direction to form an obtuse angle "D" therewith. Anterior peripheral edge surface 48 extends substantially perpendicular to the optical axis OA and forms a substantially right angle "C" with outer-most peripheral edge surface 44 at one end, and an obtuse angle "D" with the anterior concave peripheral region 46 at the other end thereof. Angle "D" is preferably between about 120 and 160 degrees, is more preferably between about 130 and 150 degrees, and is most preferably about 140 degrees. It is noted that anterior peripheral edge surface 48 is optional and in an alternate embodiment, anterior concave region 46 extends along dotted line 51 in FIG. 5 and directly intersects and forms an acute angle with outer-most peripheral edge surface 44.

In the illustrated embodiment, the anterior and posterior optic surfaces 34a, 34b are both convex. In this embodiment, the dimensions provided above are suited for an IOL across a power range of about 10 D to about 30 D. It is noted, however, that the invention is not limited to a bi-convex optic or a particular power.

In a preferred embodiment, IOL 32 is formed from acrylic and is lathed and milled in one piece from an intraocular grade acrylic button. In this method, an acrylic button is blocked (mounted) to an arbor which in turn is mounted to a lathe having a cutting tool (preferably a diamond cutting tool). The arbor is set rotating while the cutting tool lathes what will become the posterior optic surface 34b including the sharp edge 40, the posterior concave region 42, and the posterior facing surfaces of haptics 36-39. Once this step is complete, the arbor is removed from the lathe and the button is deblocked (removed) from the arbor. The button is flipped over and blocked to another arbor (posterior face down). The arbor is mounted to the lathe and set rotating while the cutting tool lathes what will become the anterior surface 34a of the optic, the anterior concave region 46, the optional anterior edge surface 48, and the anterior facing surfaces of haptics 36-39. Once this step is complete, the arbor is removed from the lathe and transferred to a milling machine. At the milling station, the arbor remains stationary while the milling tool cuts a path entirely through the button to form the complete perimeter P (outline) of the one-piece IOL (see FIG. 3). In the exemplary embodiment of IOL 32, the milling operation also cuts out the holes 36'-39' in the haptics 36-39.

Figure 6:
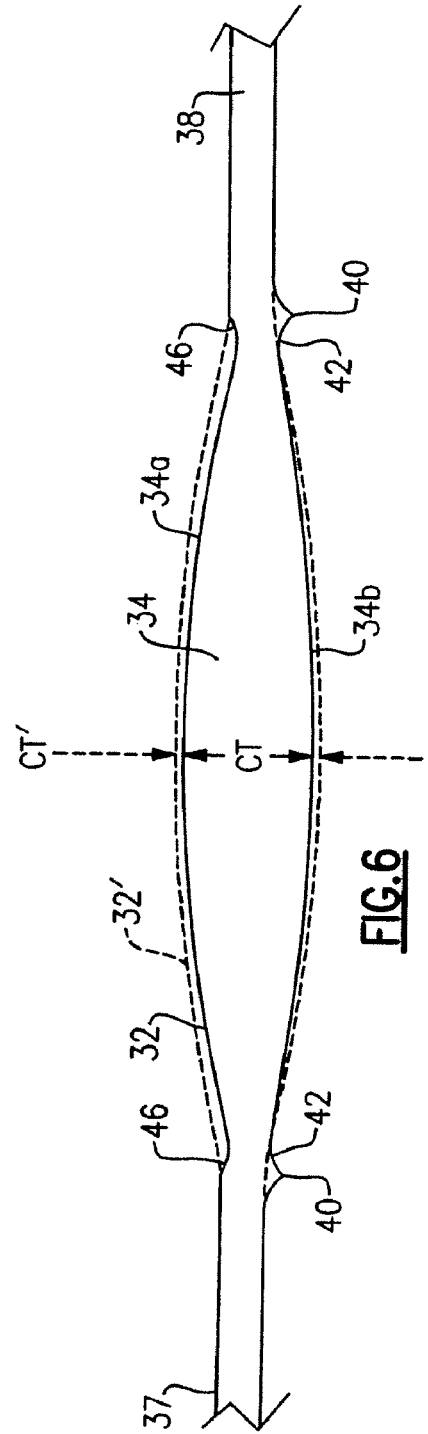
FIG. 6 is a cross-sectional view comparing a prior art IOL in dotted lines to the inventive IOL in solid lines as taken generally along the line 6-6 of FIG. 3.

Referring to FIG. 6, the reduction in area realized by the inventive IOL compared to a prior art IOL shown in dotted lines is illustrated. The center thickness CT of the inventive IOL 32 is smaller than the center thickness CT' of the prior art IOL 32', the anterior and posterior concave regions 46 and 42 have reduced the area at the periphery of the optic, and the sharp edge 40 has been formed. In a preferred embodiment, the CT of the inventive IOL 32 is between about 0.50 mm for a +10.00 D (diopter) lens and about 1.1 mm for a +30.00 D lens. The prior art IOL 32' is not able to pass through a sub-3 mm incision nor does it have any feature to inhibit or prevent PCO.

The posterior and anterior concave regions 46 and 42 are preferably located opposite each other and are of substantially the same radius where $R_1=R_2$, this radius being between about 0.15 mm and 0.5 mm, more preferably between about 0.20 mm and 0.40 mm, and most preferably is about 0.30 mm. The minimum thickness between $R_1$ and $R_2$ is designated $T_3$ and this is preferably between about 0.10 mm and 0.3 mm and is most preferably about 0.20 mm. The one or more haptics 36-39 which help stabilize the IOL in the eye are preferably spaced from the posterior limit 44p of the outer-most posterior edge surface 44. The IOL optic 34 is this reduced in size through the anterior and posterior concave regions 46 and 42 yet strength and stability of the IOL 32 is maintained. This is due at least in part to the haptic thickness $T_1$ which has not been reduced compared to prior art IOLs of similar design (see FIG. 6). Furthermore, it will be realized the optic thickness $T_3$ as measured between the anterior and posterior concave regions 46, 42 is less than the haptic thickness $T_1$. The anterior concave region 46 increases the in-situ stability of the IOL by preventing the IOL from vaulting anteriorly (i.e., toward the cornea) and thereby also helps keep the sharp edge 40 firmly indented into the posterior capsular bag wall. This creates a barrier to inward migration of LECs and PCO is thereby inhibited. The sharp edge 40 also provides additional material area to the posterior side of the IOL as compared to the anterior side of the IOL which balances the posterior concave region 42 in that the IOL will vault posteriorly despite the posterior concave region 42 which, as stated above, reduces the overall dimension of the optic 34 to allow it to be passed through a sub-3 mmm incision. In other words, while the anterior concave region 46 acts to urge the IOL to vault posteriorly, the posterior concave region 42 does not urge the IOL to vault anteriorly due to the extra material on the posterior side attributed by the posterior sharp edge 40. The spacing of the haptic 36-39 from the posterior limit 44p of the outer-most posterior edge 44 also assists in maintaining the posterior vault. Furthermore, it will be realized the optic thickness $T_3$ as measured between the anterior and posterior concave regions 46, 42 is less than the haptic thickness $T_1$ (see values given above) which also contributes to the strength and stability of the IOL in-situ.

There is thus provided a unique IOL and method of making the IOL which is small enough to fit through a sub-3 mm incision, strong enough to remain stable in the eye, and includes a sharp edge that substantially inhibits PCO as described above.

Table of Dimensions

| | |
|---|---|
| CT | Preferably between about 0.50 mm for a +10.00 D (diopter) lens and about 1.1 mm for a +30.00 D lens |
| $R_1$ and $R_2$, where $R_1$ is preferably substantially equal to $R_2$ | Preferably between about 0.15 mm and 0.5 mm, more preferably between about 0.20 mm and 0.40 mm, and most preferably is about 0.30 mm |
| $T_1$ | Preferably between about 0.20 mm and 0.40 mm, is more preferably between about 0.25 mm and 0.35 mm, and is most preferably about 0.30 mm |
| $T_2$ | Preferably between about 0.25 mm and 0.50 mm, is more preferably between about 0.30 mm and 0.40 mm, and is most preferably about 0.37 mm |
| $T_3$ | Preferably between about 0.10 mm and 0.3 mm and is most preferably about 0.20 mm |
| $H_1$ | Preferably between about 0.05 mm and 0.25 mm, is more preferably between about 0.10 mm and 0.20 mm, and is most preferably about 0.13 mm |
| Angle "A" | Preferably between about 70 and 120 degrees, is more preferably between about 80 and 100 degrees, and most preferably is about 90 degrees |
| Angle "B" | Preferably between about 110 and 150 degrees, is more preferably between about 120 and 140 degrees, and most preferably is about 130 degrees |
| Angle "C" | Preferably substantially 90 degrees |
| Angle "D" | Preferably between about 120 and 160 degrees, is more preferably between about 130 and 150 degrees, and is most preferably about 140 degrees |

The invention claimed is:

1. An intraocular lens for implanting in a human eye, comprising:
   a) a lens optic having opposite anterior and posterior optic surfaces and an optical axis extending from said anterior surface to said posterior surface;
   b) a posterior concave region located radially outwardly of said posterior optic surface;
   c) an anterior concave region located radially outwardly of said anterior optic surface;
   d) an outer-most peripheral edge surface located radially outwardly of said anterior and posterior concave regions; and
   e) a posterior sharp edge disposed between the posterior concave region and at least a portion of the outer-most peripheral edge,
   wherein the lens has a minimum distance between the posterior concave region and the anterior concave region, the minimum distance being less than a second thickness of the lens at a second location that is disposed radially outwardly of the location of the minimum distance.

2. The intraocular lens of claim 1, and further comprising at least one haptic extending from said outer-most peripheral edge.

3. The intraocular lens of claim 1 and further comprising an anterior edge surface extending substantially perpendicular to said optical axis between said anterior concave region and said outer-most peripheral edge surface.

4. The intraocular lens of claim 1 wherein said posterior optic surface is convex.

5. The intraocular lens of claim 1 wherein said anterior optic surface is convex.

6. The intraocular lens of claim 1 wherein said anterior and posterior optic surfaces are both convex.

7. The intraocular lens of claim 1 where the radius of said anterior concave region is substantially equal to the radius of said posterior concave region.

8. The intraocular lens of claim 7 wherein said anterior and posterior concave regions are located substantially opposite each other.

9. The intraocular lens of claim 8 wherein the minimum thickness "$T_3$" between said radii is between about 0.10 mm and 0.3 mm.

10. The intraocular lens of claim 2 wherein the thickness "$T_1$" of said haptic is between about 0.20 mm and 0.40 mm.

11. The intraocular lens of claim 7 wherein said anterior and posterior concave regions are located substantially opposite each other and the minimum thickness "$T_3$" between said radii is between about 0.10 mm and 0.3 mm.

12. The intraocular lens of claim 11, and further comprising at least one haptic extending from said outer-most peripheral edge of said optic.

13. The intraocular lens of claim 12 wherein said thickness "$T_3$" between said radii is less than said thickness "$T_1$" of said haptic.

14. The intraocular lens of claim 1, wherein the minimum thickness and the second thickness are measured parallel to an optical axis of the lens.

15. The intraocular lens of claim 1, wherein the second thickness is a thickness at the outer-most peripheral edge.

16. The intraocular lens of claim 1, wherein both the anterior concave region and the posterior concave region are smoothly curved.

17. The intraocular lens of claim 1, wherein the posterior concave region is posteriorly facing.

18. The intraocular lens of claim 1, wherein the posterior concave region is disposed on a posterior face of the lens and the anterior concave region is disposed on an anterior face of the lens.

19. The intraocular lens of claim 1, wherein the posterior concave region blends smoothly with the posterior optic surface, and the anterior concave region blends smoothly with the anterior optic surface.

20. An intraocular lens for implanting in a human eye, comprising:
   a) a lens optic having opposite anterior and posterior optic surfaces and an optical axis extending from said anterior surface to said posterior surface;
   b) a posterior concave region located radially outwardly of said posterior optic surface;
   c) an anterior concave region located radially outwardly of said anterior optic surface;
   d) an outer-most peripheral edge surface located radially outwardly of said anterior and posterior concave regions; and
   e) a posterior sharp edge disposed between the posterior optic surface and at least a portion of the outer-most peripheral edge,
   wherein the lens has a minimum distance between the posterior concave region and the anterior concave region, the minimum distance being less than a second thickness of the lens at a second location that is disposed radially outwardly of the location of the minimum distance.

* * * * *